(12) United States Patent
Noh

(10) Patent No.: US 8,637,095 B2
(45) Date of Patent: Jan. 28, 2014

(54) COMPOSITION FOR PREVENTING HAIR LOSS, WITH EXCELLENT HAIR STYLING FUNCTION, AND HAIR TONIC CONTAINING SAME

(76) Inventor: Hyun Soon Noh, Seoul (KR)

( * ) Notice: Subject to any disclaimer, the term of this patent is extended or adjusted under 35 U.S.C. 154(b) by 0 days.

(21) Appl. No.: 13/512,811

(22) PCT Filed: Aug. 18, 2011

(86) PCT No.: PCT/KR2011/006075
§ 371 (c)(1),
(2), (4) Date: Aug. 10, 2012

(87) PCT Pub. No.: WO2012/026708
PCT Pub. Date: Mar. 1, 2012

(65) Prior Publication Data
US 2013/0064908 A1    Mar. 14, 2013

(30) Foreign Application Priority Data
Aug. 26, 2010 (KR) .................. 10-2010-0083143

(51) Int. Cl.
*A01N 65/00* (2009.01)

(52) U.S. Cl.
USPC ............................................. 424/725

(58) Field of Classification Search
None
See application file for complete search history.

(56) References Cited

FOREIGN PATENT DOCUMENTS

| | | |
|---|---|---|
| JP | 2008273874 A | 11/2008 |
| KR | 1019980026581 A | 7/1998 |
| KR | 1020000051877 A | 8/2000 |
| KR | 1020070095077 A | 9/2007 |
| KR | 100874225 B1 | 12/2008 |
| KR | 1020090069484 A | 7/2009 |

*Primary Examiner* — Michael Meller
(74) *Attorney, Agent, or Firm* — IP Strategies

(57) ABSTRACT

An alopecia prevention composition consists of 0.1~3 weight % of salicylic acid, 0.1~5 weight % of tocopherol acetate, 0.1~3 weight % of nicotinic acid amide, 0.1~1 weight % of polyvinylpyrrolidone, 8~12 weight % of ethanol, 0.3~0.5 weight % of polyoxyethylene hydrogenated castor oil, 0.2~0.4 weight % of Sophora Angustifolia root extract, 0.2~0.4 weight % of peony root extract and a residual quantity of purified water.

8 Claims, No Drawings

COMPOSITION FOR PREVENTING HAIR LOSS, WITH EXCELLENT HAIR STYLING FUNCTION, AND HAIR TONIC CONTAINING SAME

FIELD OF THE INVENTION

The present invention relates to an alopecia prevention composition with excellent hair styling function and a hair tonic with the same, and in particular to an alopecia prevention composition with excellent hair styling function and hair tonic with the same which make it possible to maximize an alopecia prevention and hair growth effect along with an excellent hair styling function without irritating a user's skin.

BACKGROUND OF THE INVENTION

In modern society, beauty has become one of the big trends. A variety of studies are being conducted to treat men and women who are suffering psychologically from inherited alopecia or environmental alopecia and to promote the growth of hair.

The hairs of a human being are formed of 10~15 stands of hairs, each strand growing and degenerating. The hair grows and degenerates as it repeats three stages, consisting of an anagen during which hairs grow, a catagen during which metabolism becomes slow maintaining the shapes of hairs after the catagen, and a telogen during which a papilla shrinks and follicles gradually shrink, so the follicles become smaller as they are forced to move upward. The period and lifespan of the hair might change depending on a nutritional state, a disease history, heredity, constitution, hormone secretion or aging. In terms of a patient who suffers from alopecia, a hair in anagen moves to catagen and telogen, so a lot of hairs pull out as the anagen stage becomes abnormally slower. It can be observed that hairs are lost as the follicles become smaller.

The biggest causes in term of alopecia lie in an inherited cause (male hormone), and environment causes (pollution, styling agent for hairs). First of all, it is known that alopecia can be inherited, and its development depends on a male hormone. The male hormone related to alopecia is a DHT, which is an active male hormone generally activated by a 5-alpha-reduction enzyme. In addition to this cause, stress, disease, baby delivery, change of eating style, irregular life, blood circulation disorder, contagious inflammation and peroxide are related to alopecia; however, a definitive cause of alopecia is not known. As the industrialization and information era advance, the population of patients suffering from alopecia has increased, and among recent alopecia patients, there has been an increase in patients of lower age and in women patients.

According to the British Journal of Dermatology (2004; 150: 186-194), use of Minoxidil, approved by the USFDA, among a lot of other current commercial alopecia prevention agents, is known to result in blood vessel expansion prevention as exclusive potassium channel opener, to help develop from telogen to anagen, and to maintain the induced anagen hair period.

The oral medicine called Finasteride, Propecia; MSD, which inhibits the generation of dihydrotestosterone, a male hormone, by preventing the operation of 5-alpha-reduction enzyme, was approved from the USFDA, and is sold in the USA; however, the price is high, and side effects are reported, so its use is limited. In the industry, there is an urgent and strong demand for the development of medicine having hair growth effects and no side-effects as compared with the previously developed two medicines.

Alopecia prevention agents and hair growth solutions are being intensively studied, so a variety of products have come out; however, an alopecia prevention agent having excellent functionality has not been developed yet. Among developed products, there are minoxidil and propecia, which are, alopecia prevention agents that are widely used in the western countries, and a hair growth solution with an oriental herb extract that is widely used in Japan; however, their effects are not enough to prevent alopecia and promote hair growth.

Because hair gel, mousse, spray and hair tonic are all chemical products that are used to help style hair, their long-term use might irritate a user's skin, while causing alopecia.

BRIEF SUMMARY OF THE INVENTION

Accordingly, it is an object of the present invention to provide an alopecia prevention composition with an excellent hair styling function and a hair tonic with the same, which make it possible to prevent hair irritation and alopecia and to maximize the styling function.

To achieve the above objects, there is provided an alopecia prevention composition with an excellent hair styling function, comprising:

a) solvent;

b) at least one first component which is selected from the group consisting of:

salicylic acid, tocopherol acetate, nicotinic acid amide, DL-panthenol, and L-menthol; and c) a second component which is selected from the group consisting of: polyvinylcaprolactam, polyvinylpyrrolidone and quaternary polyvinylidazole.

According to a preferred embodiment of the present invention, the solvent is formed of alcohol.

According to another preferred embodiment of the present invention, the first component is at least two kinds of components which are selected from the group consisting of salicylic acid, tocopherol acetate, nicotinic acid amide, and the second component is formed of polyvinylpyrrolidone.

According to another preferred embodiment of the present invention, the entire alopecia prevention composition contains 0.1~3 weight % of salicylic acid, 0.1~5 weight % of tocopherol acetate, 0.1~3 weight % of nicotinic acid amide and 0.1~1 weight % of polyvinylpyrrolidone.

According to still another preferred embodiment of the present invention, with respect to the entire alopecia prevention composition, the composition consists of 0.1~3 weight % of salicylic acid, 0.1~5 weight % of tocopherol acetate, 0.1~3 weight % of nicotinic acid amide, 0.5~5 weight % of polyvinylpyrrolidone, 8~20 weight % of ethanol, 0.3~0.5 weight % of polyoxyethylene hydrogenerated castor oil, 0.2~0.4 weight % of Sophora Angustifolia root extract, 0.2~0.4 weight % of peony root extract and residual quantity of purified water.

According to still another preferred embodiment of the present invention, with respect to the whole alopecia prevention composition, the composition consists of 0.1~3 weight % of salicylic acid, 0.1~5 weight % of tocopherol acetate, 0.1~3 weight % of nicotinic acid amide, 0.5~5 weight % of polyvinylpyrrolidone, 8~20 weight % of ethanol, 0.3~0.5 weight % of polyoxyethylene hydrogenerated castor oil, 0.2~0.4 weight % of Sophora Angustifolia root extract, 0.2~0.4 weight % of peony root extract and residual quantity of purified water, and the Sophora Angustifolia and peony root extracts are prepared by extracting from ethanol, 1.3 butylene glycol and purified water or a mixture of them.

According to still another embodiment of the present invention, the alopecia prevention composition contains at least one conditioning agent which is selected from the group consisting of:

Sophora Angustifolia root extract, peony root extract, ginseng extract, black bean extract, green tea extract and Korean angelica extract.

According to still another embodiment of the present invention, 0.1~20 weight % of conditioning agent is included with respect to the whole alopecia prevention composition.

To achieve the above objects, there is provided a hair tonic containing an alopecia prevention composition.

The alopecia prevention composition according to the present invention makes it possible to provide an excellent hair styling function and to maximize the prevention of furuncle and dandruff of head skin and to provide the hair with luster, hair irritation prevention, and smooth hair.

DETAILED DESCRIPTION OF THE INVENTION

The present invention will be described in detail.

bECAUSE hair gel, mousse, spray, hair tonic, etc. used for the purpose of styling hair are chemicals, their long-term use might cause skin irritation and alopecia.

The present invention is basically directed to providing an alopecia-prevention composition with excellent hair styling function and a hair tonic with the same, which composition comprises a) solvent; b) at least one first component which is selected from the group consisting of salicylic acid, tocopherol acetate, nicotinic acid amide, DL-panthenol, and L-menthol; and c) a second component which is selected from the group consisting of polyvinylcaprolactam, polyvinylpyrrolidone and quaternary polyvinylidazole.

According to one aspect of the present invention, the solvent is not limited thereto once it is related to an alopecia prevention composition and/or hair styling agent; however, it is preferred that the solvent is alcohol, and more preferably, the solvent is ethanol, which is not limited thereto. The addition quantity of the solvent is not limited, but it is preferred that the quantity of solvent is 5~20 weight % with respect to the whole composition. It is apparent that the quantity of the composition can be properly adjusted by an ordinary person in the art.

According to one aspect of the present invention, the first component is at least one alopecia prevention component selected from the group consisting of salicylic acid, tocopherol acetate, nicotinic acid amide, DL-panthenol, and L-menthol. In addition, the first component used in the present invention contains one among the above-mentioned five components. Even when the used component has an alopecia prevention function, the styling function might be significantly degraded if another kind of alopecia-prevention component (zinc pyrithion, copper peptide, caffeine, biotin, etc.) is contained (refer to table 4).

It is preferred that the first component used in the present invention might be formed of at least two components selected from the group consisting of salicylic acid, tocopherol acetate, nicotinic acid amide, and more preferably, it is more efficient to mix at least two kinds of components selected from salicylic acid, tocopherol acetate and nicotinic acid amide, thus enhancing a styling function and alopecia prevention (refer to Table 4).

Preferably, 0.1~3 weight % of salicylic acid, 0.1~5 weight % of tocopherol acetate and 0.1~3 weight % of nicotinic acid amide are added as effective quantities, and more preferably, 0.4~0.6 weight % of salicylic acid, 1~3 weight % of tocopherol acetate, 0.2~0.5 weight % of nicotinic acid amide are added. If the quantities of salicylic acid, tocopherol acetate and nicotinic acid amide exceed the above-mentioned range, the styling function might decrease (refer to Table 4).

According to an embodiment of the present invention, the second component might be selected from the group consisting of polyvinylcaprolactam, polyvinylpyrrolidone and quaternary polyvinylidazole; however, polyvinylpyrrolidone is more preferably used, which is most effective to hair protection and alopecia prevention (refer to Table 4). In this case, the second component might be added as an effective component by 0.1~1 weight % with respect to the entire alopecia prevention composition, and more preferably, it is 0.4~0.7 weight %.

According to another preferred embodiment of the present invention, the alopecia-prevention composition might further comprise at least one conditioning agent selected from the group consisting of Sophora Angustifolia root extract, peony root extract, ginseng extract, black bean extract, green tea extract and Korean angelica extract.

According to further another preferred embodiment of the present invention, it is preferred that 0.3~10 weight % of the conditioning agent is added with respect to the whole composition, and more preferably, 0.3~3 weight % of it is added.

The alopecia-prevention composition according to the present invention further comprises at least one component selected from the group consisting of pH adjusting agent, moisturizer, perfume, coloring agent, antibiotic, dissolution adjuvant and ultraviolet ray block agent, and the residual quantities except for the solvent, the first component, the second component, the conditioning agent and/or other components are water (purified water). For example, the remaining quantities of 72 weight % are water when there are provided 20 weight % of the solvent, 3 weight % of the first component, 1 weight % of the second component, 3 weight % of the conditioning agent, and 1 weight % of additive.

According to another preferred embodiment of the present invention, the alopecia-prevention composition of the present invention is directed to providing a hair tonic which contains the alopecia-prevention composition as an effective component. When the composition of the present invention is formed of a hair tonic, a proper quantity of it is preferably coated for the sake of hair styling; however it is preferred that it is coated in the quantity of 1~30 mg per day for an adult.

The preferred embodiments of the present invention will be described in more detail, and the present invention is not limited thereto.

Embodiment 1

Comparison Example 4

As seen in Tables 1 to 3, the hair tonic agents of the embodiments 1 to 17 and the comparison examples 1 to 4 were prepared by mixing at room temperature the components with respect to 100 weight % of the entire compositions as shown in Tables 1 to 3 [tocopherol acetate (Roche vitamin company, BP170), salicylic acid (Duksan chemical), nicotinic acid amide Amsal Chem. Pvt. Ltd. (A-1/401/402/403, G.I.D.C., Ankleshwar, Gujarat State, India), DL-panthenol (DSM Nutritional Products LTD (Darly Ayrshire Scotland UK KA25JJ), zinc pyrithion (dispersion liquid (API CORPORATION (2-3-4, NIHONBASHT, CHUO, TOKYO, 103~0027, Japan), biotin (Taedong chemical industry company), polyvinylpyrrolidone (Krijas K-30 of Daichigogyoseiyak company), polyvinylcaprolactam (Krijas L-20 of Daichigogyoseiyak company), quaternary polyvinylidazole (Krijas S-30 of Daichigogyoseiyak company), and copper peptide (Marinoel, C-1)].

TABLE 1

| component | Embodiment 1 | Embodiment 2 | Embodiment 3 | Embodiment 4 | Embodiment 5 | Embodiment 6 | Embodiment 7 |
|---|---|---|---|---|---|---|---|
| Ethanol | 10 | 10 | 10 | 10 | 10 | 10 | 10 |
| salicylic acid | 0.5 | | | | | 0.5 | 0.5 |
| tocopherol acetate | | 2 | | | | 2 | 2 |
| nicotinic acid amide | | | 0.3 | | | 0.3 | 0.3 |
| DL-panthenol | | | | 0.5 | | 0.5 | 0.5 |
| L-menthol | | | | | 1 | 1 | |
| zinc pyrithion | | | | | | | |
| Copper peptide | | | | | | | |
| Caffeine | | | | | | | |
| Biotin | | | | | | | |
| polyvinylpyrrolidone | 0.5 | 0.5 | 0.5 | 0.5 | 0.5 | 0.5 | 0.5 |
| polyvinylcaprolactam | | | | | | | |
| quaternary polyvinylidazole | | | | | | | |
| Purified water | Residual quantity | Residual quantity | Residual quantity | Residual quantity | Residual quantity | Residual quantity | Residual quantity |

1. Good Color Stability

TABLE 2

| component | Embodiment 8 | Embodiment 9 | Embodiment 10 | Embodiment 11 | Embodiment 12 | Embodiment 13 | Embodiment 14 |
|---|---|---|---|---|---|---|---|
| Ethanol | 10 | 10 | 10 | 10 | 10 | 10 | 10 |
| salicylic acid | 0.5 | 0.5 | | | 0.5 | 0.5 | 0.5 |
| tocopherol acetate | 2 | 2 | 2 | 2 | 2 | 2 | 2 |
| nicotinic acid amide | 0.3 | | 0.3 | | 0.3 | 0.3 | 0.3 |
| DL-panthenol | | | | 0.5 | | | |
| L-menthol | | | | | | | |
| zinc pyrithion | | | | | | | |
| Copper peptide | | | | | | | |
| Caffeine | | | | | | | |
| Biotin | | | | | | | |
| polyvinylpyrrolidone | 0.5 | 0.5 | 0.5 | 0.5 | | | 0.25 |
| polyvinylcaprolactam | | | | | 0.5 | | 0.25 |
| quaternary polyvinylidazole | | | | | | 0.5 | |
| Purified water | Residual quantity | Residual quantity | Residual quantity | Residual quantity | Residual quantity | Residual quantity | Residual quantity |

TABLE 3

| component | Embodiment 15 | Embodiment 16 | Embodiment 17 | Comparison example 1 | Comparison example 2 | Comparison example 3 | Comparison example 4 |
|---|---|---|---|---|---|---|---|
| Ethanol | 10 | 10 | 10 | 10 | 10 | 10 | 10 |
| salicylic acid | 4 | 0.5 | 0.5 | 0.5 | 0.5 | 0.5 | 0.5 |
| tocopherol acetate | 2 | 7 | 2 | 2 | 2 | 2 | 2 |
| nicotinic acid amide | 0.3 | 0.3 | 04 | 0.3 | 0.3 | 0.3 | 0.3 |
| DL-panthenol | | | | | | | |
| L-menthol | | | | | | | |
| zinc pyrithion | | | | 1 | | | |
| Copper peptide | | | | | 0.5 | | |
| Caffeine | | | | | | 0.8 | |
| Biotin | | | | | | | 0.7 |
| polyvinylpyrrolidone | 0.5 | 0.5 | 0.5 | 0.5 | 0.5 | 0.5 | 0.5 |
| polyvinylcaprolactam | | | | | | | |
| quaternary polyvinylidazole | | | | | | | |
| Purified water | Residual quantity | Residual quantity | Residual quantity | Residual quantity | Residual quantity | Residual quantity | Residual quantity |

Test Example

The following tests were performed with respect to the hair tonic prepared based on the above-mentioned embodiments 1 to 17 and the above-mentioned comparison examples 1 to 4, the result of which is shown in Table 4.

The hair tonic was stored in a glass sample bottle and was left at a temperature of 35° C. for one month, and the state of the composition was observed with naked eyes.

Criteria of Evaluation

◯: No changes were observed.

Δ: Partial separation from water was observed.

x: Definite separation was observed.

2. Test of Coating Performance when Coated on Hair 5 subjects were randomly gathered, and each hair tonic was applied three times at a room temperature, and the application performances were evaluated with respect to coating of hair. The evaluation of the application performance with respect to coating of hair was conducted based on the following 5-score criteria, the subjects recorded subjective scores, and the average of the scores was calculated.

[Evaluation Criteria]

5 points: when coated on hair, it applied very well along with foam phases and felt very good to the touch.

4 points: when coated on hair, it applied well along with foam phases and felt good to the touch.

3 points: when coated on hair, it applied not bad along with foam phases and felt not bad to the touch.

2 points: when coated on hair, it did not apply well along with foam phases and felt bad to the touch.

1 points: when coated on hair, it applied very badly along with foam phases and felt very bad to the touch.

effects were evaluated based on a 10-point is score, the average of the scores was calculated, and the result is shown in Table 4.

4. Skin Irritation Evaluation 50 subjects were gathered randomly, each hair tonic was used for six months, and skin irritation levels were evaluated.

5 points: no skin irritation
4 points: almost skin irritation
3 points: a little skin irritation
2 points: skin irritation occurred
1 points: severe skin irritation Alopecia Prevention Effects Tests regarding alopecia-prevention effects were performed with respect to 35 subjects who had initial stages of the alopecia phenomenon. The hair tonic of embodiments 2, 8 and 1 were used two times per day for 8 weeks, and after 8 weeks passed, the hair of the subjects was washed. The hairs that fell off during the hair washing were collected and counted, and the result is shown in Table 4.

TABLE 4

| | Good color stability | Application performance | Styling performance | Duration force | Luster | Hair protection | Skin irritations | Alopecia prevention |
|---|---|---|---|---|---|---|---|---|
| Embodiment 1 | ○ 4.2 | 4.3 | 4.3 | 4.0 | 3.8 | 3.7 | | |
| Embodiment 2 | ○ 4.1 | 4.4 | 4.1 | 4.2 | 3.9 | 3.9 | | 43.7 |
| Embodiment 3 | ○ 4.2 | 4.2 | 4.5 | 4.2 | 3.7 | 3.8 | | |
| Embodiment 4 | ○ 3.6 | 3.8 | 3.9 | 3.8 | 3.8 | 3.9 | | |
| Embodiment 5 | ○ 3.8 | 3.7 | 3.8 | 3.7 | 3.7 | 3.6 | | |
| Embodiment 6 | ○ 3.5 | 3.3 | 3.2 | 3.3 | 4.4 | 4.5 | | |
| Embodiment 7 | ○ 3.7 | 3.6 | 3.6 | 3.5 | 4.5 | 4.4 | | |
| Embodiment 8 | ○ 4.3 | 4.2 | 4.4 | 4.1 | 4.5 | 4.4 | | 36.9 |
| Embodiment 9 | ○ 4.0 | 4.3 | 4.2 | 4.0 | 4.1 | 4.0 | | |
| Embodiment 10 | ○ 4.1 | 4.2 | 4.4 | 4.2 | 4.2 | 4.1 | | |
| Embodiment 11 | ○ 3.7 | 3.6 | 3.7 | 3.6 | 4.1 | 4.3 | | |
| Embodiment 12 | ○ 4.2 | 4.3 | 4.5 | 4.0 | 3.7 | 3.8 | | 58.1 |
| Embodiment 13 | ○ 4.0 | 4.2 | 4.4 | 4.1 | 3.5 | 3.7 | | |
| Embodiment 14 | ○ 4.1 | 4.3 | 4.2 | 4.2 | 4.2 | 4.1 | | |
| Embodiment 15 | ○ 4.0 | 3.9 | 4.2 | 4.0 | 4.5 | 4.3 | | |
| Embodiment 16 | ○ 3.8 | 4.0 | 4.1 | 3.9 | 4.4 | 4.2 | | |
| Embodiment 17 | ○ 3.8 | 4.0 | 4.0 | 4.1 | 4.2 | 4.1 | | |
| Comparison example 1 | Δ 2.9 | 3.0 | 3.2 | 3.5 | 4.3 | 4.4 | | |
| Comparison example 2 | Δ 3.2 | 3.1 | 3.2 | 3.6 | 4.4 | 4.3 | | |
| Comparison example 3 | ○ 3.2 | 3.1 | 3.3 | 3.5 | 4.2 | 4.1 | | |
| Comparison example 4 | ○ 3.9 | 3.9 | 3.8 | 3.9 | 4.2 | 4.2 | | |

3. Evaluation of Styling 50 subjects were randomly gathered, and each hair tonic was used three times. The hair-styling performance, the duration of the shaping force, luster of the hair and hair protection As shown in Table 4, good color stability, application performance, styling performance, duration, luster, etc. of the hair tonic composition of embodiments 1 to 17 of the present invention were significantly better than those of the hair tonic composition of the comparison examples 1 to 4. In addition, the effects of the hair tonic composition of embodiment 8, in which salicylic acid, tocopherol acetate and nicotinic acid amide are mixed properly, were most excellent. The hair protection, skin irritation and the alopecia-prevention effects of embodiment 8, in which the polyvinylpyrrolidone was used solely, were much better than those of embodiments 12 to 14, in which another kind of hair styling composition was used.

Preparation Examples

The hair tonics shown in Table 5 were prepared.

TABLE 5

| Name of materials | Combined quantities (g) |
|---|---|
| salicylic acid | |
| tocopheryl acetate | |
| nicotinic acid amide | |
| Ethanol | |
| Polyoxyethylene hydrogenerated castor oil | |
| Sophora Angustifolia root extract | |
| peony root extract | |
| Ginseng extract | |
| Black beam extract | |
| Green tea extract | |
| Korean angelica extract. | |
| Citric acid | |
| Combined perfumes | |
| Purified water | |
| polyvinylpyrrolidone | |

The effective components of the Sophora Angustifolia root extracts were extracted such that 500 g of the dried Sophora Angustifolia was added to 70% ethanol, which was four times in terms of weight (kg) basis, which mixture was then heated at 80° C. for 2 hours. The extracts were left at a room temperature for one day and were precipitated for removal of foreign substances. The extracts were filtered two times using filter paper, and the filtered extracts were fully vaporized using a vacuum evaporator, thus preparing the Sophora Angustifolia root extracts. The extracts of black bean, the peony root extract, the ginseng, the green tea and the Korean angelica extract were extracted in the same manner as the Sophora Angustifolia root extracts.

INDUSTRIAL APPLICABILITY

Since the present invention can achieve both hair styling functions and alopecia prevention effects, the present invention can be very useful to the hair styling industry.

The invention claimed is:

1. An alopecia treatment composition, consisting essentially of:
   0.1~3 weight % of salicylic acid,
   0.1~5 weight % of tocopherol acetate,
   0.1~3 weight % of nicotinic acid amide,
   0.1~1 weight % of polyvinylpyrrolidone,
   8~12 weight % of ethanol,
   0.3~0.5 weight % of polyoxyethylene hydrogenerated castor oil,
   0.2~0.4 weight % of Sophora Angustifolia root extract,
   0.2~0.4 weight % of peony root extract, and
   a residual quantity of purified water.

2. A hair tonic consisting essentially of the alopecia treatment composition of claim 1.

3. A method of making the alopecia treatment composition of claim 1, consisting essentially of:
   extracting Sophora Angustifolia root extracts by
      adding dried Sophora Angustifolia root to ethanol,
      heating the dried Sophora Angustifolia root and ethanol mixture at 84° C. for 2 hours,
      leaving the heated Sophora Angustifolia root mixture at room temperature for one day,
      precipitating the Sophora Angustifolia root mixture to remove foreign substances, producing an extract,
      filtering the Sophora Angustifolia root extract, and
      vaporizing the filtered Sophora Angustifolia root extract using a vacuum evaporator, thereby concentrating and preparing the Sophora Angustifolia root extracts, and
   preparing a peony root extract by
      adding dried peony root to ethanol,
      heating the peony root and ethanol mixture at 80° C. for 2 hours,
      leaving the heated peony root mixture at room temperature for one day,
      precipitating the peony root mixture to remove foreign substances,
   producing an extract,
      filtering the peony root extract, and
      vaporizing the filtered extract using a vacuum evaporator, thereby concentrating and preparing the peony root extracts, to yield the composition of claim 1.

4. An alopecia treatment composition, consisting essentially of:
   0.1~3 weight % of salicylic acid,
   0.1~5 weight % of tocopherol acetate,
   0.1~3 weight % of nicotinic acid amide,
   0.5~5 weight % of polyvinylpyrrolidone,
   8~20 weight % of ethanol,
   0.3~0.5 weight % of polyoxyethylene hydrogenerated castor oil,
   0.2~0.4 weight % of Sophora Angustifolia root extract,
   0.2~0.4 weight % of peony root extract, and
   a residual quantity of purified water.

5. A hair tonic, consisting essentially of the alopecia treatment composition of claim 4.

6. A method of making the alopecia treatment composition of claim 4, consisting essentially of:
   extracting Sophora Angustifolia root extracts by
      adding dried Sophora Angustifolia root to ethanol,
      heating the dried Sophora Angustifolia root and ethanol mixture at 80° C. for 2 hours,
      leaving the heated Sophora Angustifolia root mixture at room temperature for one day,
      precipitating the Sophora Angustifolia root mixture to remove foreign substances, producing an extract,
      filtering the Sophora Angustifolia root extract, and
      vaporizing the filtered Sophora Angustifolia root extract using a vacuum evaporator, thereby concentrating and preparing the solid Sophora Angustifolia root extracts, and
   preparing a peony root extract by
      adding dried peony root to ethanol,
      heating the peony root and ethanol mixture at 80° C. for 2 hours,
      leaving the heated peony root mixture at room temperature for one day,
      precipitating the peony root mixture to remove foreign substances,
   producing an extract,
      filtering the peony root extract, and
      vaporizing the filtered extract using a vacuum evaporator, thereby concentrating and preparing the peony root extracts, to yield the composition of claim 4.

7. An alopecia treatment composition, consisting essentially of:
- 0.1~3 weight % of salicylic acid,
- 0.1~5 weight % of tocopherol acetate,
- 0.1~3 weight % of nicotinic acid amide,
- 0.5~5 weight % of polyvinylpyrrolidone,
- 8~20 weight % of ethanol,
- 0.3~0.5 weight % of polyoxyethylene hydro generated castor oil,
- 0.2~0.4 weight % of Sophora Angustifolia root extract,
- 0.2~0.4 weight % of peony root extract, and
- a residual quantity of purified water,
- wherein said Sophora Angustifolia root and peony root extracts are prepared by extraction using a solvent selected from the group consisting of ethanol, 1,3 butylene glycol, purified water, and mixtures thereof.

8. A hair tonic, consisting essentially of the alopecia treatment composition of claim 7.

* * * * *